(12) United States Patent
Axelgaard et al.

(10) Patent No.: US 6,950,688 B2
(45) Date of Patent: Sep. 27, 2005

(54) DUAL ELEMENT SENSOR MEDICAL ELECTRODE

(75) Inventors: Jens Axelgaard, Fallbrook, CA (US); Steve Heard, Escondido, CA (US)

(73) Assignee: Axelgaard Manufacturing Company. Ltd., Fallbrook, CA (US)

( * ) Notice: Subject to any disclaimer, the term of this patent is extended or adjusted under 35 U.S.C. 154(b) by 207 days.

(21) Appl. No.: 10/407,720

(22) Filed: Apr. 4, 2003

(65) Prior Publication Data

US 2003/0220553 A1 Nov. 27, 2003

Related U.S. Application Data

(63) Continuation-in-part of application No. 09/714,594, filed on Nov. 16, 2000, now abandoned.

(51) Int. Cl.[7] ................................................. A61B 5/04
(52) U.S. Cl. ........................ 600/391; 600/392; 600/396
(58) Field of Search ................................ 600/391, 392, 600/394, 396; 607/149, 152, 153

(56) References Cited

U.S. PATENT DOCUMENTS

| | | | | | |
|---|---|---|---|---|---|
| 3,518,984 A | * | 7/1970 | Mason | ........................ | 600/392 |
| 3,911,906 A | * | 10/1975 | Reinhold, Jr. | ................ | 600/392 |
| 3,993,049 A | * | 11/1976 | Kater | ........................... | 600/391 |
| 4,267,840 A | * | 5/1981 | Lazar et al. | .................... | 606/32 |
| 4,300,575 A | * | 11/1981 | Wilson | ........................ | 607/152 |
| 4,554,924 A | * | 11/1985 | Engel | .......................... | 600/391 |
| 4,580,339 A | * | 4/1986 | Ioffe | ........................... | 600/391 |
| 4,635,642 A | * | 1/1987 | Cartmell et al. | ............. | 600/392 |
| 4,640,289 A | * | 2/1987 | Craighead | .................... | 600/391 |
| 4,848,353 A | * | 7/1989 | Engel | .......................... | 600/391 |
| 4,934,383 A | * | 6/1990 | Glumac | ....................... | 607/152 |
| 5,660,892 A | * | 8/1997 | Robbins et al. | .............. | 427/537 |
| 5,782,761 A | * | 7/1998 | Gusakov | ...................... | 600/391 |
| 6,434,410 B1 | * | 8/2002 | Cordero et al. | ............. | 600/396 |
| 6,687,524 B1 | * | 2/2004 | Svejk | .......................... | 600/391 |
| 2004/0082843 A1 | * | 4/2004 | Menon | ........................ | 600/395 |

* cited by examiner

*Primary Examiner*—Lee S. Cohen
(74) *Attorney, Agent, or Firm*—Walter A. Hackler

(57) ABSTRACT

A medical sensor electrode includes an electrically conductive adhesive for establishing electrical contact with a mammalian body to enable the electrode to monitor physiological electrode potentials from the body. A first sensor element includes a flexible electrically conductive plate disposed on the conductive adhesive with the plate having substantial smaller dimension that the dimension of the conductive adhesive. A second sensor element includes an electrical conductive member disposed over the first sensor element and adhesive. The conductive member includes a non-conductive sheet coated with multiple layers of a metal and metal halide. A non-conductive backing is disposed over the second sensor element and conductive adhesive with the backing and the second sensor element having apertures for providing access to the first sensor element. A lead wire is connected to the first sensor element through the backing and the second sensor element and a non-conductive label is disposed over the backing apparatus and end of the lead wire.

23 Claims, 2 Drawing Sheets

DUAL ELEMENT SENSOR MEDICAL ELECTRODE

The present application is a continuation-in-part of U.S. Ser. No. 09/714,594 filed Nov. 16, 2000, now abandoned.

The present invention generally relates to the field of disposable biomedical electrodes for establishing an electrical connection between the skin and an electro-medical apparatus. More specifically, the present invention relates to a semi-disposable biomedical electrode used in conjunction with monitoring equipment for producing Electroencephalograms (EEG), Electromyograms (EMG), Electrocardiographs (ECG) and the like.

EEG's are used to help diagnose the presence and type of seizure disorders, confusion, head injuries, brain tumors, infections, degenerative diseases, and metabolic disturbances that affect the brain. They are also used to evaluate sleep disorder and to investigate periods of unconsciousness; furthermore, EEGs may be used to confirm brain death in a comatose patient.

EMG's are recording of muscle activity signals and changes of these signals used for evaluation of the muscles.

ECG's are recorded traces of physiological electric potentials corresponding to muscular activity of the heart muscle. The traces provide a diagnostic tool for detecting heart disease and defects. Such monitoring of physiological electrical potentials may be employed in a number of other applications. ECG traces may be utilized in a number of different situations. For example, a simple ECG test may be used in order to obtain a single tracing for diagnostic purposes, which can be carried out in a few minutes in a physician's office. Hence, medical electrodes utilized for such testing may be of a relatively simple disposable variety, since they are only in service for a very short time.

However, patients hospitalized in an intensive care ward or other specialized care unit may require continuous, extended monitoring. Such medical electrodes may be required to remain in service for many days. Consequently, longer-term monitoring applications require that the electrode adheres well and conducts electrically consistently over extended periods of time.

Present medical electrode designs are not suitable for service over a period of many days. In addition, lack of electrode flexibility inhibits electrode performance. For example, electrodes have relatively hard, bulky sensor components which make them uncomfortable. This is particularly true in the case of infants. Also the bulky sensor component and lead wire attachment is of relatively weak construction, and accordingly subject to separation, which results in interrupted monitoring signals.

As hereinabove briefly noted, electrodes for monitoring infants must be designed for specific conditions; for example, the premature birth of a baby (neonate) often leads to an underdevelopment of the heart. Such a condition must be monitored continuously. In addition, respiration monitoring is also important in neonatal care because such babies are subject to apnea, i.e., sudden loss of respiration.

A neonate is typically born having a low body temperature and is unable to self regulate its body temperature, and requires an incubator. A neonate incubator is a device consisting of a rigid boxlike enclosure in which a neonate may be kept in a controlled environment for medical care. The device may include; a heater, a fan to circulate the warmed air, a container for water to add humidity, a control valve though which oxygen may be added, and access ports for nursing care.

Given the fragile nature of a prematurely born baby and the challenging incubator environment, requirements for a monitoring electrode are demanding and numerous. For example, a hygroscopic hydrogel conductive adhesive used to attach an electrode to a neonatal is likely to absorb water from the surrounding humid environment until it is saturated. At this point, the hydrogel will loose its adhesive tack and separate from the skin of the neonate, resulting in loss of the electrical trace.

Prior art construction of medical electrodes for neonatal monitoring includes a hard and bulky sensing element. The hard and bulky sensing element poses a problem when the neonatal patient is placed on the stomach or chest and the neonate is laying directly on the hard and bulky sensing element. The applied pointed pressure put directly on the chest cavity could lead to an uncomfortable feeling for the neonate. Furthermore, an additional shortfall in traditional medical electrodes for neonatal monitoring is the marginal quality electrical trace provided.

The relatively high impedance level found in traditional medical electrodes reduces the quality of the electrical trace obtained through the monitoring of the physiological electric potentials from the body of a neonate, thereby making diagnosing more difficult.

The mechanical bonding of the lead wire in prior art electrodes is typically done by gluing or by pressing the lead wire onto the sensor element within the electrode, however, this is a very inconsistent method of attaching the lead wire. The inconsistency of attaching the lead wire to the sensor may result in lead wire separation causing a critical situation as no vital signs are monitored until the electrode is exchanged with a properly operating electrode. This is of particular importance with neonatal electrodes because long leads are necessitated by the incubator.

The present invention overcomes the above-mentioned shortfalls and provides for a relatively inexpensive electrode having sensor elements that are thin and flexible which allows for electrode chest placement without the concern of applying pressure on the chest cavity while placing the neonate on the chest. Further, an electrode in accordance with the present invention, provides better electrical trace quality due to lower impedance. This enables a quicker diagnosis. The second sensor element may preferably be porous, thus enabling water evaporation therethrough which enables any excess water to evaporate. For situations where water absorption is not desired, an impermeable backing may be used. In addition, the hydrogel utilized in the present invention may be optimized for use in a challenging incubator environment, by making the hydrogel less receptive to absorbing water, thus providing a secure electrical connection for the sensor.

The components of the present invention further lend to economic production of a superior electrode.

SUMMARY OF THE INVENTION

A medical sensor electrode in accordance with the present invention generally includes an electrically conductive adhesive for establishing electrical contact with a mammalian body, thereby enabling the medical sensor electrode to monitor the physiological electric potentials from the body.

A first sensor element is provided, which includes a flexible electrically conductive plate disposed on the adhesive with the plate having substantially smaller dimensions than the dimensions of the adhesive. A second sensor element is provided which includes an electrically conductive member disposed over the first sensor element and the adhesive. The member has dimensions approximately equal to the adhesive dimensions, and the member further includes an aperture therethrough for providing access to the first sensor element.

The aperture in the second sensor element has dimensions smaller than the first sensor element dimensions in order to secure the first sensor element between the second sensor element and the conductive adhesive with the conductive adhesive adhering to and providing electrical contact with both sensor elements.

A non-conductive backing is provided and disposed over the second sensor element with the backing also having an aperture, which has dimensions smaller than the aperture in the second sensor element, therethrough and aligned with the second sensor element aperture, for providing access to the first sensor element. A lead wire may be electrically and physically connected to the first sensor element through the second element and backing apertures. A non-conductive label is disposed over the backing aperture and the lead wire to protect and prevent undesired contact therewith.

More specifically, both the second sensor element and backing may be porous in order to provide for moisture evaporation therethrough. In this manner, the electrode becomes a breathing electrode that prevents excessive water buildup in the adhesive which may lead to separation of the electrode from the body.

In one embodiment of the present invention, the second sensor element may comprise a non-conductive medium coated with multiple layers of a conductive medium including a metal and a metal halide, or combinations thereof in the form of an ink or the like. Preferably, the multiple layers include a layer of silver with a layer of silver and silver chloride disposed therein. The first sensor element may comprise a silver foil, and preferably the adhesive contains a halide. This halide in combination with silver chloride ink, in the second sensor, enables rapid re-polarization of the electrodes subsequent to defibrillation potentials which may be applied to the body.

BRIEF DESCRIPTION OF THE DRAWINGS

The advantages and features of the present invention will be more clearly understood when taken in conjunction with the accompanying drawings in which.

DETAILED DESCRIPTION

Figure 1:
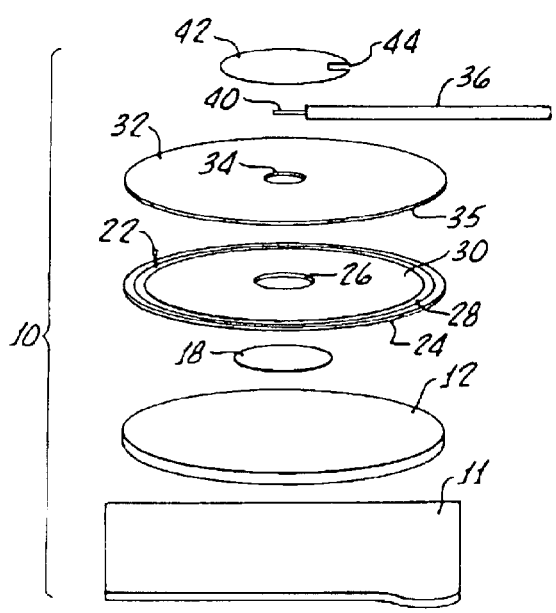
FIG. 1 is an exploded perspective view of the electrode in accordance with the present invention and generally showing two sensor elements, an adhesive, a backing and a lead wire.
Figure 2:
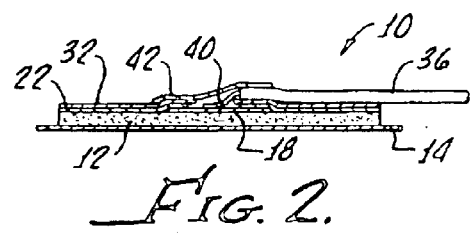
FIG. 2 is a cross-sectional view of the electrode shown in FIG. 1 as it may be assembled.
Figure 3:
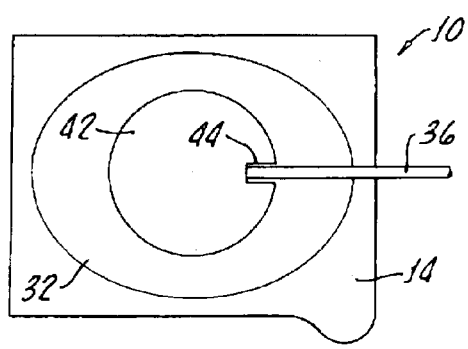
FIG. 3 is a plan view of the electrode shown in FIGS. 1–2.

With reference to FIGS. 1–3, there is shown an electrode 10 in accordance with the present invention generally including an electrically conductive adhesive 12 for establishing electrical contact with a mammalian body (not shown) for enabling the medical sensor electrode 10 to monitor or sense physical electric potentials or other bioelectric events from the body.

The adhesive 12 is preferably a highly conductive hydrogel composition comprising a uniform aqueous solution within a hydrophilic cross-linked polymer. Typical thicknesses are from between about 0.025 inches to about 0.040 inches with a volume resistivity of less than about 500 ohm-cm. Suitable hydrogels for use in the present invention are taught in U.S. Pat. Nos. 5,868,136, 6,038,464 and 6,115,625. All of these patents and patent application are incorporated in their entirety herewith by this specific reference thereto for teaching the types of adhesive, a gel, suitable for use in the present invention. In order to provide an electrode 10 suitable for neonatal care, the adhesive 12 may be formulated to maximize adhesion durability in a humid environment. A suitable formulation is as follows:

| INGREDIENTS | PERCENT |
|---|---|
| D.I Water | 10–15% |
| CaCl2 | 1–3% |
| KCl | 2–5% |
| 50% Sodium AMPS | 0–20% |
| Glycerin | 20–90% |
| 50% NaOH solution | 0.5–2.0% |
| PEG - 300 | 0–10% |
| PVP - K90 | 0.5–6.0% |
| PVP/VA W-735 | 1–5% |
| NVP | 2–3% |
| Irgacure 2959 | 0.1–0.3% |
| EGDMA | 0.05–0.20% |
| Tin Octoate | 0.05–0.20% |
| Acrylic Acid | 8–12% |

A release film 14 is also provided for preventing contact with the adhesive 12 until use of the electrode 10.

A first sensor element or plate 18 is disposed on the adhesive 12 and, as shown, the first sensor element or plate 18 has substantially smaller dimensions than dimensions of the adhesive 12. The first sensor element 18 may be a silver foil having a thickness between about 0.0005 inches to about 0.0080 inches, with a preferred thickness of about 0.001 inches. It should be appreciated that the element, or plate, 18 may be of any rectilinear shape, such as, for example, a circle, rectangular, strip, ellipse, etc.

While silver is a preferred metal, other metals may also be utilized, as hereinafter noted. Alternate materials for the first sensor element 18 would include any film material, conductive by nature or made conductive by applying any conductive media, for example, a conductive ink loaded with either silver or combination of silver, silver chloride partials or carbon. The plate 18 adhesion to the gel 12 provides for positive electrical coupling therebetween as well as acting as a receiver of electrical potentials from the body (not shown) through the conductive adhesive 12.

A second sensor element 22, includes a non-conductive sheet 24 coated with ink layers composed of silver and/or silver chloride powder dispersed in a polymer matrix dissolved in a solvent and dried. The second sensor element 22 is disposed over the first sensor element 18 and the adhesive 12. The sheet 24 may be a fabric which can be a woven, knitted, spun bonded, wet laid or otherwise disposed natural or synthetic fiber matrix.

More particularly, the sheet/fabric 24 may be coated with a first thin core layer 28 of an ink composed of silver powder dispersed in a polymer matrix dissolved in a solvent. Thereafter, the layer 28 may be coated with a second thin shell layer 30 of an ink composed of silver and silver chloride powder dispersed in a polymer matrix dissolved in a solvent and dried. Usable ranges of the dry components in the ink are between about 80% to about 90% by weight silver of which about 5% to about 25% is silver chloride. The remainder is binding resin which can be composed of a natural or synthetic resin such as, for example, acrylic, polyamide, styrene, styrene maleic anhydride, cellulosics and the like. The invention is not limited to a silver/silver chloride combination but rather any suitable metal/metal halide may be used, such as, for example, a first layer 28 of tin and a second layer 30 of tin chloride.

As a specific example the silver layer, or core, 28 may be formed from an ink formulation having about 86% silver flake and about 14% binder (resin plus plasticizer) and the silver/silver chloride layer 30, or shell, may be formed from an ink formulation having about 73% silver flake, about 13% silver chloride and about 14% binder (resin plus plasticizer). Each layer 28, 30 may be disposed with about 0.002 Kg per square foot on the sheet 24.

The element 22 has dimensions approximately equal to the adhesive dimensions and includes an aperture 26 for providing access to the first sensor 18 through the second sensor element 22. The aperture 26 has dimensions smaller that the first sensor element 18 in order to secure the first sensor element between the second sensor element and the conductive adhesive. The conductive adhesive bonds to and provides electrical contact with both sensor elements 18, 22.

A typical sheet material may have a thickness of between about 0.001 inch to about 0.100 inches. A preferred thickness is about 0.005 inches. It has been discovered that a layer of silver 28, and a layer of 30 of silver/silver chloride thereover on the sheet provide for greatly improved electrical performance over a single layer of silver/silver chloride of greater thickness.

For example, with a single coat (not shown) of silver/silver chloride the surface impedance of the sheet is in the range of 3 to 10 ohm, whereas with two layers, i.e. a coat 28, of silver, and thereover a coat 30 of silver and silver chloride, having less thickness than the single coat, the surface impedance of the sheet 22 is in the 1 ohm range. An improvement by a factor of at least three. The layers 28, 30 are separately applied and dried in a conventional manner.

An important consideration, particularly with respect to long-term monitoring such as in stress testing, during surgery, or during in-patient monitoring, is the recovery of the trace following the defibrillation in which a relatively large externally generated electrical potential of short duration provided to the patient is necessary in situations to cause a fibrillating heart to return to normal activity.

The electrode 10 may be utilized in an electrocardiograph device and sudden application of a large electrical potential will cause considerable disturbance in the electrocardiogram trace. In the present invention, defibrillization recovery is enhanced by the silver/silver chloride chemical reaction involving the silver chloride on the second sensing element 22 and the halide, preferably chloride, of the conductive adhesive 12. This reaction tends to dissipate the electrical charge relatively rapidly. Rapid dissipation of such electrical charge is important in order that a physician can obtain immediate feedback on the state of the patient's heart.

A non-conductive backing 32 is disposed over the second sensor element 22 with the backing 32 having an aperture 34 therethrough for providing access to the first sensor element 18, the backing aperture 34 is smaller than aperture 26 in the second sensor element 22 allowing adhesive 35 on the backing 32 to bond to the first sensor element 18, the backing aperture 34 and second sensor aperture being aligned for this purpose.

A suitable backing material includes a porous non-woven polyester member coated with an adhesive and having an overall thickness of between 0.001 inches to about 0.100 inches. A preferred thickness is about 0.007 inches. Alternative materials would include any porous or non-porous film or fiber member. Preferably a porous material is utilized which, in combination with the porous second sensor element, enables evaporation of water through the electrode 10 which prevents excessive water buildup in the adhesive 12.

This in turn insures positive contact between the adhesive 12 and the body without undesirable separation over long periods of time. An electrical lead wire 36 is provided and is electrically and physically connected to the first sensor element 18 through the second sensor element aperture 26 and the backing aperture 34. Connection of an end 40 of the lead wire is preferably made by a solder, weld or fused connection 38 to the first sensor element 18. This connection provides a solid anchor suitable for supporting long lead wires 36 as is necessary for neonatal electrodes 10.

Covering the lead wire end 40 and aperture 34, is a non-conductive label 42. A typically label 42 material includes a vinyl or paper coated with an adhesive on one side and having an overall thickness of between 0.001 inches to about 0.01 inches. Preferably the thickness is 0.0045 inches and the label 42 includes a notch 44 for accommodating the lead wire 36.

Figure 4:
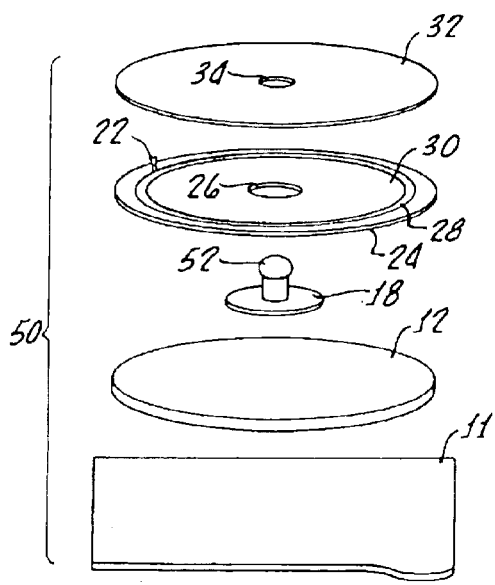
FIG. 4 is an exploded perspective view of an alternative embodiment in accordance with the present invention.
Figure 5:
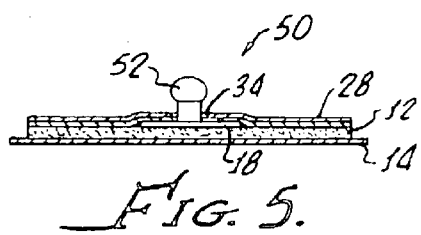
FIG. 5 is a cross-sectional view of the embodiment shown in FIG. 4.
Figure 6:
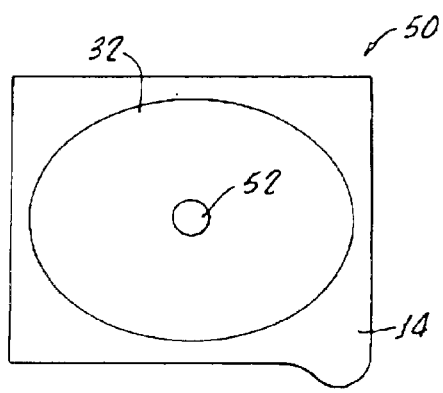
FIG. 6 is a plan view of the embodiments shown in FIGS. 4–5.

With reference to FIGS. 4–6 there is shown an alterative embodiment electrode 50 in accordance with the present invention. Common reference characters in FIGS. 4–6 represent identical or substantially similar components as hereinbefore described in connection with the electrode 10 shown in FIGS. 1–3.

The electrode 50 includes a connector 52 attached to the first sensor 18 that extends through the apertures 26, 34 for enabling electrical communication therewith.

Figure 7:
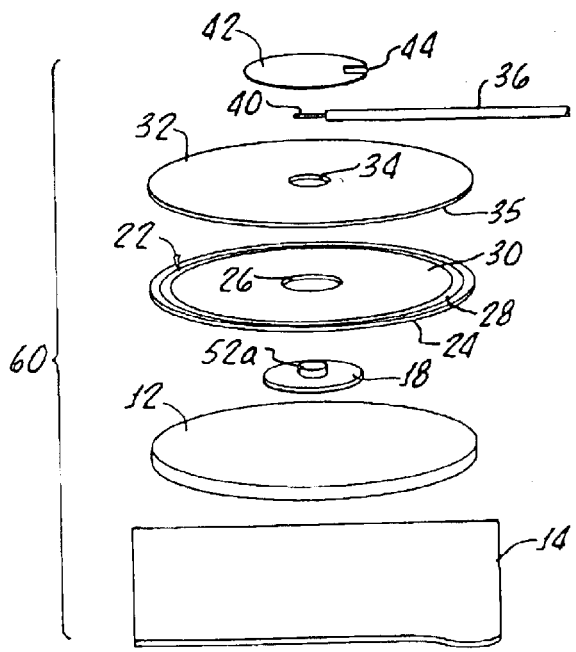
FIG. 7 is an alternative embodiment of the present invention.

A similar electrode embodiment 60 utilizes a stud connector 52 a and lead wire 36 is shown in FIG. 7. Common reference characters in FIGS. 1 and 7 represent identical components as described. The lead wire end 40 may be melted or fused to the connector 52a in a manner flattening the connector to provide a low profile. In that regard, the connector 52 a is preferably formed from a carbon filled plastic coated with a layer of Ag/AgCl and the melt/fuse connection with the lead 40 may be by any suitable method, such as heat or ultrasound.

Electrode Performance

Figure 8:
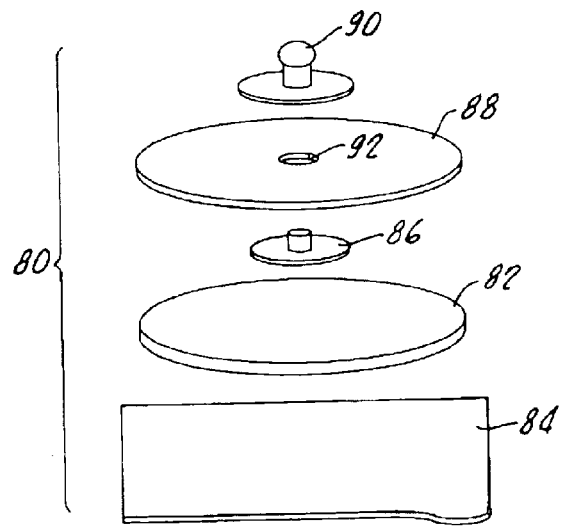
FIG. 8 is a typical prior art electrode used in a comparison study.

For comparison, the electrical performance of the present electrodes 10, 50, 60 is measured with that of a common design electrode 80, shown in FIG. 8. The prior art electrode includes a conductive adhesive 82, as in electrode 50, along with a release film 84, and a sensor element 86, backing 88 and connector 90 attached to the sensor through an aperture 92 in the backing 88. All components are of the same material of construction and size as the electrode 50. The results are as follows:

The electrical performance of electrodes was evaluated in order to determine its electrical responses for use as a medical electrode, according to the proposed standards for disposable ECG electrodes by The Association for the Advancement of Medical Instrumentation. (American National Standard for Disposable ECG Electrodes, Association for the Advancement of Medical Instrumentation, ANSI/AAMI EC12-2000, May 13th 2000 Revision).

Two identical electrodes are joined together, hydrogel back to hydrogel back, to form an electrode pair. This electrode pair is then tested on an electrode tester Xtratek ET-65A commonly used to characterize the performance of monitoring electrodes. The measured items were DC offset after 60 seconds, AC impedance at 10 Hz, Simulated Defibrillation Recovery (SDR) after 5 seconds and the highest slope of SDR for the 4th pulse. The specification standards mandated by AAMI are also shown in Table-1.

TABLE 1

|  | Present Invention | Prior Art | AAMI Standards |
| --- | --- | --- | --- |
| DC Offset | 0.1 mV | 0.5 mV | Less than 100 mV |
| AC Impedance | 30 ohms | 200 ohms | Less than 2000 ohms |
| SDR | 5.5 mV | 15 mV | Less than 100 mV |
| SLOPE | 0.1 mV/s | 0.5 mV/s | Absolute value is less than 1.0 mV/s |

The invention in particular demonstrates significant improvements in the electrode impedance (AC Impedance). The lower electrode impedance enhances the monitoring of physiological electric potentials from the body of mammals, assisting in more accurate diagnoses.

Although there has been hereinabove described a specific dual element sensor medical electrode in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclose herein. Accordingly, any and all modifications, variations or equivalent arrangements which may occur to those skilled in the art, should be considered to be within the scope of the present invention as defined in the appended claims.

What is claimed is:

1. A neonate medical sensor electrode comprising:
   an electrically conductive adhesive for enabling electrical contact with a neonate thereby enabling the medical sensor electrode to monitor physiological electric potentials from the neonate, the adhesive being formulated to maximize adhesion durability in an incubator;
   a first sensor element comprising a electrically conductive plate disposed on the adhesive, the plate having substantially smaller dimensions than dimensions of the adhesive;
   a second sensor element comprising an electrically conductive member is disposed over said first sensor element and adhesive, the member having dimensions approximately equal to the adhesive dimensions, the member having an aperture therein for providing access to said first sensor element through said second sensor element, said aperture having dimensions smaller than the first sensor element dimensions in order to secure said first sensor element between said second sensor element and the adhesive, the adhesive adhering to and providing electrical contact with both sensor elements, said second sensor element comprising a non-conductive medium coated with multiple layers of a conductive medium;
   a non-conductive backing disposed over said second sensor element, the backing having an aperture therethrough for providing access to said first sensor element, the backing aperture and second sensor element aperture being aligned with one another;
   a low profile connection comprising a lead wire electrically and physically connected to said first sensor element through the second sensor element and backing apertures, said connection being below a top surface of said second sensor element to reduce pressure on the neonate; and
   a non-conductive label disposed over the backing aperture and an end of the lead wire.

2. The medical sensor electrode according to claim 1 wherein said multiple layers comprises multiple layers of Ag and AgCl.

3. The medical sensor electrode according to claim 2 wherein a layer of Ag and AgCl is disposed over a layer of Ag.

4. The medical sensor electrode according to claim 3 wherein said second sensor element is porous.

5. The medical sensor electrode according to claim 3 wherein said second sensor element is non-porous.

6. The medical sensor electrode according to claim 3 wherein the backing is porous.

7. The medical sensor electrode according to claim 3 wherein the backing is non-porous.

8. The medical sensor electrode according to claim 7 wherein said first sensor element comprises a flexible silver foil.

9. A medical sensor electrode according to claim 1 further comprising a connector for interconnecting said lead wire with said first sensor, said connector comprising a carbon filled plastic coated with a layer of Ag/AgCl.

10. The medical sensor electrode according to claim 1 wherein the adhesive comprises a hydrogel.

11. The medical sensor electrode according to claim 1 wherein the adhesive formulation comprises:

| INGREDIENT | PERCENT |
| --- | --- |
| D.I Water | 10–15% |
| CaCl2 | 1–3% |
| KCl | 2–5% |
| 50% Sodium AMPS | 0–20% |
| Glycerin | 20–90% |
| 50% NaOH solution | 0.5–2.0% |
| PEG - 300 | 0–10% |
| PVP - K90 | 0.5–6.0% |
| PVP/VA W-735 | 1–5% |
| NVP | 2–3% |
| Irgacure 2959 | 0.1–0.3% |
| EGDMA | 0.05–0.20% |
| Tin Octoate | 0.05–0.20% |
| Acrylic Acid | 8–12%. |

12. A neonate medical sensor electrode comprising:
   an electrically conductive adhesive for establishing electrical contact with a neonate thereby enabling the medical sensor electrode to monitor physiological electrical potentials from the neonate, the adhesive comprising a hydrogel containing a halide and formulated to maximize adhesion durability in an incubator;
   a first sensor element comprising an electrically conductive plate disposed on the adhesive for sensing the electrical potentials, the plate having substantially smaller dimensions than dimensions of the adhesive;
   a second sensor element comprising an electrically conductive member disposed on the adhesive for sensing the electrical potentials, the member having dimensions approximately equal to the adhesive dimensions and comprising, as an electrically conductive medium, multiple layers of Ag and AgCl dispersed across the medium for repolarizing the electrode subsequent to defibrillation potentials applied to the body;

an electrical low profile connector, for connecting the electrical potentials to a monitor, said connector being below a top surface of said second sensor element to reduce pressure on the neonate; and a non-conductive backing for covering the electrical sensors.

13. The medical sensor electrodes according to claim 12 wherein said second sensor is disposed over said first sensor.

14. The medical sensor electrode according to claim 13 wherein said second sensor includes an aperture, said aperture being aligned with said first sensor and having dimensions smaller than said first sensor.

15. The medical sensor electrode according to claim 14 wherein said electrical connector is attached to the first sensor through the aperture.

16. The medical sensor electrode according to claim 12 wherein said second sensor element is porous.

17. The medical sensor electrode according to claim 12 wherein said second sensor element is non-porous.

18. The medical sensor electrode according to claim 12 wherein the backing is porous.

19. The medical sensor electrode according to claim 12 wherein the backing is non-porous.

20. The medical sensor electrode according to claim 12 wherein the second sensor element comprises a non-conductive medium coated with a layer of Ag and a layer of Ag/AgCl.

21. The medical sensor electrode according to claim 12 wherein said first sensor element comprises a flexible silver foil.

22. A medical sensor electrode according to claim 12 wherein said electrical connector comprises a carbon filled plastic coated with a layer of Ag/AgCl.

23. The medical sensor electrode according to claim 12 wherein the adhesive formulation comprises:

| INGREDIENT | PERCENT |
| --- | --- |
| D.I Water | 10–15% |
| CaCl2 | 1–3% |
| KCl | 2–5% |
| 50% Sodium AMPS | 0–20% |
| Glycerin | 20–90% |
| 50% NaOH solution | 0.5–2.0% |
| PEG - 300 | 0–10% |
| PVP - K90 | 0.5–6.0% |
| PVP/VA W-735 | 1–5% |
| NVP | 2–3% |
| Irgacure 2959 | 0.1–0.3% |
| EGDMA | 0.05–0.20% |
| Tin Octoate | 0.05–0.20% |
| Acrylic Acid | 8–12%. |

* * * * *